United States Patent
D'elia et al.

(10) Patent No.: US 6,692,644 B2
(45) Date of Patent: Feb. 17, 2004

(54) PROCESS FOR RECOVERING OIL AND SULFONATES FROM FILTRATION PANEL

(75) Inventors: Luigi D'elia, Pandino-Cremona (IT); Orazio Pianta, Milan (IT)

(73) Assignee: Agip Petroli S.p.A., Rome (IT)

( * ) Notice: Subject to any disclaimer, the term of this patent is extended or adjusted under 35 U.S.C. 154(b) by 0 days.

(21) Appl. No.: 10/110,236

(22) PCT Filed: Dec. 18, 2000

(86) PCT No.: PCT/EP00/13060

§ 371 (c)(1),
(2), (4) Date: Apr. 23, 2002

(87) PCT Pub. No.: WO01/44261

PCT Pub. Date: Jun. 21, 2001

(65) Prior Publication Data

US 2003/0098284 A1 May 29, 2003

(30) Foreign Application Priority Data

Dec. 17, 1999 (IT) ......................................... MI99A02619

(51) Int. Cl.⁷ ................................................. B01D 12/00
(52) U.S. Cl. ...................... 210/772; 210/773; 210/777; 210/791; 210/792; 203/91; 494/37
(58) Field of Search ................................. 210/768, 769, 210/772, 773, 777, 791, 797, 800, 787, 789, 792; 494/37; 203/91

(56) References Cited

U.S. PATENT DOCUMENTS

| 3,155,616 A | 11/1964 | Voorhees |
| 3,155,617 A | 11/1964 | Voorhees |
| 3,213,131 A | 10/1965 | Benedict |
| 3,537,966 A | 11/1970 | Holst et al. |
| 3,537,996 A | 11/1970 | Holst et al. |
| 4,225,509 A | 9/1980 | Seth |
| 4,501,670 A | 2/1985 | Tyson et al. |
| 4,614,597 A | 9/1986 | Stuart et al. |

FOREIGN PATENT DOCUMENTS

| WO | WO 97/46443 | 12/1997 |

*Primary Examiner*—Robert J. Popovics
(74) *Attorney, Agent, or Firm*—Oblon, Spivak, McClelland, Maier & Neustadt, P.C.

(57) ABSTRACT

Process for treating filtration panels obtained by the filtration of oils containing sulfonates of earth-alkaline metal, the above filtration being carried out in the presence of filter aids essentially consisting of siliceous material, which comprises: (a) dilution of the filtration panel with a $C_4$–$C_8$ aliphatic hydrocarbon, preferably hexane, and addition of another filter aid, thus obtaining a suspension of the panel and of the filter aid in the aliphatic hydrocarbon; (b) filtration of the suspension of step (a), thus obtaining a solid essentially consisting of filter aid with a minimum content of sulfonate and a turbid $C_4$–$C_8$ hydrocarbon solution (i); (c) centrifugation of the turbid hydrocarbon solution (i), thus obtaining a solid and a purified hydrocarbon solution (ii); (d) treatment of the purified hydrocarbon solution (ii) with means suitable for eliminating the $C_4$–$C_8$ hydrocarbons, thus recovering the sulfonate of earth-alkaline metal.

16 Claims, No Drawings

PROCESS FOR RECOVERING OIL AND SULFONATES FROM FILTRATION PANEL

The present invention relates to a process for recovering oil and sulfonates from filtration panels.

Oil-soluble sulfonates of earth-alkaline metals are widely used as detergent additives for lubricating oils. They are obtained by sulfonating hydrocarbon mixtures with a high content of aromatic alkyl hydrocarbons, characterized by a long lateral alkyl chain bound to the aromatic ring.

The hydrocarbon mixture can be of synthetic origin (and therefore consisting of aromatic alkyl hydrocarbons produced by the alkylation of benzene with a polymer of propylene) or it can derive from heavy refinery distillates characterized by a high content of aromatic alkyl hydrocarbon. Typical heavy refinery distillates suitable for the purpose have a weight average molecular weight of about 480.

As far as synthetic products are concerned, these can sometimes have a lower molecular weight, but the weight average molecular weight is higher than 400.

The sulfonic acids produced in the sulfonation process are then converted into sulfonates of earth-alkaline metals.

The conversion of sulfonic acids to sulfonates of earth-alkaline metals can be effected by direct neutralization with a base compound of earth-alkaline metal, such as hydroxide, oxide or carbonate. This conversion can also be carried out by the neutralization of sulfonic acids with a hydroxide of an alkaline metal; the alkaline metal sulfonate thus formed is then converted to sulfonate of earth-alkaline metal by metathesis with a compound of earth-alkaline metal such as hydroxide, oxide, carbonate, chloride.

The sulfonates can be neutral salts obtained by the reaction of sulfonic acids with the stoichiometric quantity required for neutralizing acids, or they can be overbased. Overbased sulfonates can be prepared by means of contact of sulfonic acids (or salts of the alkaline metals of the above acids) with an excess, with respect to the stoichiometric value, of a base compound of earth-alkaline metal. The process consists in mixing the sulfonic acid (or its metal alkaline salt) with an excess of base earth-alkaline compound, usually in the presence of a hydrocarbon solvent, and introducing gaseous carbon dioxide into the mixture. An alcohol is commonly used to promote the production of over-based sulfonate.

The process to which the present invention refers is well known to experts in the field, see for example "Procédé de suralcalinisation d'additifs détergents: "RÔle des Promoteurs et determination du régime de la réaction de surbasage" R. Gallo and F Jacquet, Revue de l'Institut Francais du Petrol, Vol. 476, Nr. 2, Mars-Avril 1991.

The final step of the production process of neutral or overbased sulfonates is the separation of the desired products from the by-products, particularly non-reacted compounds of earth-alkaline metals and sediments. It is important for the detergent additive to have a colloidal structure with sufficiently small particle dimensions (usually <0.1 micron) so as to be transparent to visible light (see U.S. Pat. No. 3,155,617) and easily filterable through the usual filtering devices. In fact, if particles of non-reacted alkaline or earth-alkaline material are present in the additive, or if almost insoluble large dimensional colloidal structures have been created in the synthesis phase, without a suitable liquid-solid separation step, abrasions and decantation can occur when using the lubricating oil.

The purification step can be carried out before or after the removal of the reaction solvents.

The end additive proves to consist of a mixture of sulfonate (overbased) formed and of the lubricating base added during the process to lower the viscosity. In the case of overbased additives, the basicity reserve, measured by TBN according to the procedure described in WO 97/46443, depends not only on the ratios between the reagents but also on the dilution with the lubricating base.

The purification step of the additives based on sulfonates usually consists of a filtration with aids. The material to be removed is normally made up of the non-reacted base oxide or hydroxide, impurities of the starting oxide or hydroxide consisting of carbonates of the metal itself or oxides or hydroxides of other metals, sulfonates deriving from the neutralization of the sulfuric acid optionally present in sulfonic acids, crystalline carbonates formed during the reaction, unstable micelles of sulfonate (sediment) formed during the reaction which prove to be non-oil-soluble owing to the considerable dimensions of the carbonate nucleus and/or of an insufficient coating thereof on the part of the surface-active agent based on sulfonate.

The content of "sediment" in the product to be filtered varies according to the synthesis process, the raw materials used and degree of overbasicity required, and it is mainly this impurity which determines the filtration rate and quantity of filter aid to be used U.S. Pat. No. 3,537,996 identifies "considerable quantities of solids prevalently consisting of colloidal particles of calcium carbonate having large dimensions, not dispersible in the oily medium (sediment)", as main impurities to be eliminated by filtration. U.S. Pat. No. 3,155,616 describes how some processes for producing colloidal dispersions of calcium carbonate which use sulfonates, are made difficult by the presence of materials which tend to deteriorate upon contact with the hot surfaces of the process equipment, forming agglomerates of large dimensional particles which cannot be tolerated in the end lubricating product and which can only be removed with great difficulty due to their substantial non-filterability.

In solid-liquid purification by filtration, U.S. Pat. No. 3,537,996 identifies amorphous diatomaceous siliceous earth as a suitable aid, both for forming the precoat on the filtration surface and to be added to the product to be purified, and indicates a quantity of 1 to 15% in the product to be purified as appropriate. U.S. Pat. No. 3,155,617 also specifies diatomaceous earth as suitable aid and lists known commercial types, such as Filter-Cel, Hy-Flo, Super Cel and Dicalite.

During the filtration process with aids, a filtration panel is produced which contains impurities present in the reaction product, the filter aid and the detergent additive. In particular the content of additive in the panel is very high and is comparable to that of the aid.

The filtration panels obtained in the processes described above should be discharged as undesired by-products of the sulfonation process. This causes a loss in oil and sulfonate. In addition, a more important factor is that these filtration panels are classified as potentially dangerous materials, with obvious disposal problems.

The necessity is therefore felt for improving the purification process of sulfonate, thus avoiding disposal of the above panels.

To solve this problem, U.S. Pat. No. 4,614,597 treats the filtration panel with acid selected from phosphoric acid and sulfuric acid until reaching a pH ranging from 2 to 7, and maintaining the mixture thus obtained at a temperature of over 150° F. The hot mixture is subsequently left to rest until separation of the two phases, the upper phase containing oil and the sulfonate, the lower phase containing the filter aid and the acid.

U.S. Pat. No. 4,501,670 on the other hand, describes a process in which the filtration panels are mixed with hot aqueous solutions of materials selected from hydroxides of alkaline metals, salts of alkaline metals of acids having ionization constants of less than $1.5 \cdot 10^{-4}$ and relative mixtures. After the separation has been completed at temperatures of over 160° F., two phases are separated which are recovered.

Both processes of the prior art reduce or eliminate the dangerousness of the panel, but have the disadvantage of requiring subsequent washing and neutralization phases. In addition, these phases do not allow the starting additive to be recovered, but rather an intermediate to be recycled, for example sulfonic acid to be recycled to the synthesis process of sulfonates, in the case of U.S. Pat. No. 4,614,597, or sodium sulfonate to he reconverted to calcium sulfonate in the case of example 1 of U.S. Pat. No. 4,501,670. This makes the process less economic.

In addition, the separation of the oily phase, containing the intermediate recovered, from the aqueous phase, containing the filter aid, is carried out by decanting, with the possibility of forming stable emulsions which can negatively influence the operating times.

A process has now been found which overcomes the drawbacks described above.

In accordance with this, the present invention relates to a process for treating filtration panels obtained by the filtration of oils containing sulfonates of earth-alkaline metal, the above filtration being carried out in the presence of filter aids essentially consisting of siliceous material, preferably diatomaceous earth, which comprises:

(a) dilution of the filtration panel with a $C_4$–$C_8$ aliphatic hydrocarbon, preferably hexane, and addition of another filter aid, thus obtaining a suspension of the panel and of the filter aid in the aliphatic hydrocarbon;

(b) filtration of the suspension of step (a), thus obtaining a solid essentially consisting of filter aid with a minimum content of sulfonate and a turbid $C_4$–$C_8$ hydrocarbon solution (i);

(c) centrifugation of the turbid hydrocarbon solution (i), thus obtaining a solid and a purified hydrocarbon solution (ii);

(d) treatment of the purified hydrocarbon solution (ii) with means suitable for eliminating the $C_4$–$C_8$ hydrocarbons, thus recovering the sulfonate of earth-alkaline metal.

The filtration panel, subsequently subjected to the process of the present invention, essentially consists of about 50% of oil, sulfonate and reaction residues, and the remaining 50% of the filter aid.

In step (a) of the process of the present invention, the above panel is treated with a quantity of hydrocarbons selected from those ranging from $C_4$ to $C_8$, preferably n-hexane, and with a filter aid of the silicon type, preferably diatomaceous earth. The weight ratio between $C_4$–$C_8$ hydrocarbons and panel is not determinant for the process of the present invention. In the preferred embodiment however, the weight ratio panel/$C_4$–$C_8$ hydrocarbons ranges from 1/0.5 to 1/20, more preferably from 1/1 to 1/10, even more preferably from 1/2 to 1/5.

As far as the quantity of filter aid added is concerned, the weight ratio between the panel and filter aid ranges from 1/0.2 to 1/5, more preferably from 1/0.4 to 1/3, even more preferably from 1/0.6 to 1/1.5.

The three components (panel, hydrocarbons, filter aid) are preferably mixed at a temperature ranging from 15° C. to 40° C., for a time sufficient to obtain good contact between the various components. Using appropriate stirring devices, a few minutes are usually sufficient.

Step (b) consists in the filtration of the suspension of step (a). Filtration devices well known to experts in the field can be used for the purpose. The use of filter presses is particularly effective. The filtration produces a turbid hydrocarbon filtrate (i) and the filter aid which proves to have a minimum content of sulfonate.

Step (c) of the process of the present invention consists in the centrifugation of the turbid hydrocarbon solution (i), the centrifugation being carried out using the usual centrifuges commercially available (laboratory, or pilot plant or industrial). When operating on an industrial scale, a centrifuge of the disc-stack type in the self-cleaning version, with an opening bowl for the discharge of the solids accumulated, or a centrifuge of the disc-stack type with continuous discharge of the solids, can be used.

This step produces a solid and a purified hydrocarbon solution (ii).

The above solid mostly consists of organic material with a micelle structure not oil-soluble in a paraffinic environment (sediment). Part of the solid on the other hand consists of inorganic material of various origins, which is very fine and not withheld in the filtration step (b).

As far as the inorganic part is concerned, this usually consists (a) partly of very fine inorganic material not withheld by the filtration and deriving from filter aids (for example silica and titanium dioxide); (b) partly of non-converted reagents (for example calcium hydroxide); (c) partly of impurities of the starting raw materials; (d) partly of non-colloidal material formed during the synthesis (for example calcium carbonate).

The final step of this process (step d) consists in eliminating the hydrocarbon solvent from the purified hydrocarbon solution (ii). This step can be carried out according to the known techniques for example distillation at atmospheric pressure or at reduced pressure. As will be shown further on in the experimental part, this step allows a sulfonated product equal to the reaction product, to be recovered.

The following examples are provided for a better illustration of the present invention.

The comparative examples show how a simple treatment consisting of (a) dilution of the panel with hexane in the presence of another filter aid, (b) filtration of the suspension thus obtained, is not sufficient.

COMPARATIVE EXAMPLE 1

In this example a filtration panel is used, coming from an industrial plant for the production of overbased sulfonate at TBN 300 starting from synthetic sulfonic acids and calcium hydroxide. The filtration is carried out, after removal of the solvents, by adding to 100 parts of the product to be purified, 3 parts by weight of siliceous aid. A precoat of aid is deposited onto the filtering surface and, at the end of the operation, the panel impregnated with product and sediments is automatically discharged by centrifugal force; on an average, 50% by weight of the panel consists of additive. The above panel (200 grams) is stirred with n-hexane (800 grams) for 10 minutes at room temperature (20–22° C.) in a 1500 ml cylindrical container equipped with a stirrer having a flat-blade turbine. 200 grams of diatomaceous earth are then added and the mixture is stirred for a further 15 minutes.

The suspension thus obtained is subjected to filtration on a bomb filter on which a cloth has been deposited, followed by a precoat of aid by the percolation of a slurry of 30 grams of diatomaceous earth in 150 ml of hexane. The filtration is carried out at a differential pressure of 1 bar, obtaining a turbid yellow-coloured hexane filtrate and a panel of about 7 cm. The hexane filtrate has a content of sediments, determined by centrifugation immediately after the filtration, ranging from 0.5 to 0.6% by volume. The additive recovered by distillation from the hexane solution, has a content of initial sediments, determined according Lo the regulation ASTM D2273, of 4% by volume, against a maximum limit allowed of 0.1% volume in the normal production product. As is known to experts in the field, the high content of sediments makes the additive recovered unsuitable for use in lubricating oils.

The yield to sulfonate (referring to % weight of the sulfonate passed into the hexane solution and subsequently recovered by distillation of the solvent, with respect to the weight of the industrial panel) is 38%. As the content of additive of the industrial panel treated is about 50% by weight, the yield to sulfonate recovered with respect to the theoretical value is about 76%.

COMPARATIVE EXAMPLE 2

N-hexane (800 grams), followed by diatomaceous earth (70 grams) are added to the same panel as example 1 (200 grams). After stirring, the mixture is filtered using the same procedure as described in comparative example 1. These operations, with the addition of 70 grams of diatomaceous earth instead of the 200 grams of comparative example 1, are repeated 10 times, slowly accumulating the solids separated in the filtrations and the filtrated hexane solutions. A sample of the overall hexane solution, subjected to distillation to remove the hexane, provided an additive with a content of initial sediments of 4% volume.

This result, as also that of comparative example 1, shows how the use of a volatile paraffinic solvent does not allow, with extraction and filtration operations alone, the production of an additive having a quality comparable to that obtained with normal production.

COMPARATIVE EXAMPLE 3

N-hexane (800 grams) and diatomaceous earth (70 grams) are added to a panel coming from a different run of the same industrial plant as comparative example 1 (300 grams).

The suspension is filtered using the same procedure as described in comparative example 1. These operations were repeated 10 times, slowly accumulating the solids separated in the filtrations and the filtrated hexane solutions. Also in this case a sample of the overall hexane solution, after removing the solvent, provided an additive with a high content of initial sediments, equal to 6% volume.

Consideration With Respect to Comparative Examples 1–3

Comparative examples 1–3 clearly demonstrate how the process which comprises the addition of n-hexane and filter aid and subsequent filtration, is not satisfactory. In fact, the sulfonate has an unacceptable content of sediments.

EXAMPLE 4

The hexane solution obtained after the filtration described in comparative example 2 is subjected to centrifugation (flow-rate 1.8 l/min) using an Alfa-Laval pilot centrifuge model LAB102 B25.

The pilot plant consists of a cylindrical reactor equipped with a stirrer, from which the LAB 102 B25 centrifuge is fed by gravity, at room temperature; the feeding flow-rate is controlled by observing the shift times of the volumes. The volumetric flow-rate control is important for constructing the correlation between the feeding flow-rate and the quality of the product recovered; from this experimental report and from a knowledge of the scale factor between the pilot centrifuge and commercial centrifuge, it is possible to estimate the quality of the industrial product.

The solvent is removed from the centrifuged hexane solution by heating to 130° C., at 100 mbar of residual pressure, for 1 hour.

The sulfonate recovered after the centrifugation is characterized according to the same methods adopted for commercial sulfonate. The results are indicated in Table 1.

EXAMPLE 5

The hexane solution obtained after the filtration described in comparative example 3 is subjected to centrifugation (flow-rate 3 l/min) using an Alfa-Laval centrifuge model LAB102 B25.

The solvent is removed from the centrifuged hexane solution by heating to 130° C., at 100 mbar of residual pressure, for 1 hour.

The sultanate recovered after the centrifugation is characterized according to the same methods adopted for commercial sulfonate. The results are indicated in Table 1.

TABLE 1

| Characteristic | Method | Unit | Commercial product (min/max.) | Commerc. product | Ex. 4 | Ex. 5 |
| --- | --- | --- | --- | --- | --- | --- |
| Density 15° C. | ASTM D1298 | kg/cm$^3$ | 1070/1130 | 1097 | 1105 | 1104 |
| Viscosity 100° C. | ASTM D445 | mm$^2$/s | 60/100 | 72.5 | 91.25 | 90.7 |
| Flash point | ASTM D93PM | ° C. | 160 min. | 181 | 170 | 173 |
| Calcium | ASTM D4927 | weight % | 11.4/12.0 | 11.47 | 11.75 | 11.7 |
| Soap | ASTM D3409 | weight % | 28 min. | 29.8 | 30 | 29.7 |
| TBN | ASTM D2896 | mg KOH/g | 295/305 | 299 | 304 | 304 |
| Init. sedim | ASTM D2273 | volume % | 0.1 max. | 0.01 | 0.005 | 0.005 |
| Large sedim. | ASTM D2273 | volume % | 0.2 max. | 0.06 | 0.01 | 0.005 |
| Haze | MEDD011 | NTU | 20 max. | 12 | 7 | 9.9 |
| Water | ASTM D95 | weight % | 0.4 max. | 0.2 | 0.2 | 0.1 |

Comments on the Data of Table 1 Relating to Examples 4–5

The data of table 1 relating to examples 4–5 clearly demonstrate that the sulfonates recovered after centrifugation, coming from filtration panels of different industrial runs, comply with the specifications of the commercial product. In addition the sulfonates recovered have a much lower haze value than the main sulfonate and are not bad-smelling.

The equality of the three products is confirmed by the relative I.R spectra.

EXAMPLE 6

Analyses were carried out on the solids separated by filtration in comparative example 3, the industrial panel treated in the same example, the diatomaceous earth used as filter aid, the sediments withheld by the LAB 102 B25 centrifuge during the treatment, described in example 5, of the hexane solution produced in comparative example 3.

The results, in terms of elemental analysis, are indicated in table 2; all the quantitative measurements were carried out in duplicate to evaluate the deviation of the measurements. The qualitative and quantitative elemental analysis of the heavy metals was carried out, after acid mineralization, by means of a Thermo Optek IRIS simultaneous inductive plasma emission spectrometer (ICP).

TABLE 2

|  | Ca % | S % | Al % | Fe % |
|---|---|---|---|---|
| Diatomaceous earth | 0.9 | 0.042 | 2.07 | 1.92 |
| Industrial panel | 12 | 1.07 | 0.67 | 0.59 |
| Solid after step (b) | 7.4 | 0.35 | 0.86 | 0.72 |
| Sediment retained by the centrifuge | 9.2 | 0.84 | 0.23 | 0.17 |

The data of table 2 demonstrate how steps (a) and (b) of the present invention allow a solid material recovered after filtration, to be obtained with a sulfur content 2.85 lower than the original industrial panel.

The same samples of table 2 were analyzed with infrared using an FTIR Bruker Equinox 55 spectrometer and an ATR (Attenuated Total Reflection) Specac Golden Gate accessory. The spectra result from the sum of 128 scans with a resolution equal to 4 $cm^{-1}$. The results are indicated in table 3. Among others, the aliphatic C—H stretch bands (CH, $CH_2$, $CH_3$) at 3000–2700 $cm^{-1}$ and the Si—O stretch band at 1068 $cm^{-1}$, were taken into consideration.

The use of the ATR technique does not allow normalization of the spectra with respect to a standard quantity of sample, and consequently the results of table 3 are in the form of a ratio between the area of aliphatic hydrocarbons and the area of $SiO_2$, this ratio being indicative of the concentration of hydrocarbons in the silicon aid.

TABLE 3

| Species | Aliph. CH (1) | $SiO_2$ (2) | Area ratio (1)/(2) |
|---|---|---|---|
| Band | 3100-2700 | 1068 |  |
| Diatomaceous earth | 0 | 86 | 0 |
| Industrial panel | 34 | 95 | 0.358 |
| Solid after step (b) | 14 | 94 | 0.149 |
| Sediments retained by the centrifuge | 35 | 94 | 0.372 |

It can be observed in table 3 how the treatment of the industrial panel, according to steps (a) and (b) of the process of the present invention, allows the indicative ratio of the concentration of hydrocarbons in the solids recovered in step (b) to be reduced 2.4 times, with respect to the original industrial panel.

The results of tables 1 to 3 demonstrate how the process of the present invention allows an additive having a quality comparable to those of normal production to be recovered from filtration panels, at the same time reducing the content of sulfur and hydrocarbons in the solids to be disposed of.

What is claimed is:

1. A process for treating filtration panels obtained by the filtration of oils containing sulfonates of earth-alkaline metal, wherein said filtration is performed in the presence of one or more siliceous filter aids, and said process comprises:

(a) diluting the filtration panel with a $C_4$–$C_8$ aliphatic hydrocarbon and adding an additional siliceous filter aid, thus obtaining a suspension of the panel and the filter aids in the aliphatic hydrocarbon;

(b) filtering the suspension of (a), thus obtaining a solid essentially consisting of the filter aids with a minimum content of sulfonate and a turbid $C_4$–$C_8$ hydrocarbon solution (i);

(c) centrifuging the turbid hydrocarbon solution (i), thus obtaining a solid and a purified hydrocarbon solution (ii);

(d) treating the purified hydrocarbon solution (ii) with a means for eliminating the $C_4$–$C_8$ hydrocarbons, thus recovering the sulfonate of earth-alkaline metal.

2. The process according to claim 1, wherein the siliceous filter aid in (a) is diatomaceous earth.

3. The process according to claim 1, wherein the $C_4$–$C_8$ hydrocarbon solvent is n-hexane.

4. The process according to claim 1, wherein in (a) the weight ratio between the filtration panel and the $C_4$–$C_8$ hydrocarbon ranges from 0.05 to 2.

5. The process according to claim 4, wherein in (a) the weight ratio between the filtration panel and the $C_4$–$C_8$ hydrocarbon ranges from 0.1 to 1.

6. The process according to claim 5, wherein in (a) the weight ratio between the filtration panel and the $C_4$–$C_8$ hydrocarbon ranges from 0.2 to 0.5.

7. The process according to claim 1, wherein the weight ratio between the filtration panel and the filter aid ranges from 0.2 to 5.

8. The process according to claim 7, wherein the weight ratio between the filtration panel and the filter aid ranges from 0.33 to 2.5.

9. The process according to claim 8, wherein the weight ratio between the filtration panel and the filter aid ranges from 0.66 to 1.66.

10. The process according to claim 1, wherein (a) further comprises mixing at a temperature ranging from 15° C. to 40° C.

11. The process according to claim 1, wherein said centrifuging is accomplished using a disc-stack centrifuge with an opening bowl for discharge of accumulated solids.

12. The process according to claim 11, wherein said disc-stack centrifuge is self-cleaning.

13. The process according to claim 1, wherein said centrifuging is accomplished using a disc-stack centrifuge with continuous discharge of accumulated solids.

14. The process according to claim 1, wherein said treating comprises distillation.

15. The process according to claim 14, wherein said distillation is at atmospheric pressure.

16. The process according to claim 14, wherein said distillation is at a sub-atmospheric pressure.

* * * * *